United States Patent [19]

Vincent et al.

[11] Patent Number: 5,190,923

[45] Date of Patent: Mar. 2, 1993

[54] PEPTIDE COMPOUNDS CONTAINING A CYCLIC AMIDE STRUCTURE

[75] Inventors: Michel Vincent, Bagneux; Georges Remond, Versailles; Bernard Portevin, Elancourt; Yolande Herve, Puteaux; Jean Lepagnol, Chatou, all of France

[73] Assignee: Adir Et Compagnie, Courbevoie, France

[21] Appl. No.: 710,283

[22] Filed: Jun. 4, 1991

[30] Foreign Application Priority Data

Jun. 18, 1990 [FR] France ............... 90 07559

[51] Int. Cl.$^5$ .................. C07K 5/04; C07K 5/06; A61K 37/02
[52] U.S. Cl. .................. 514/19; 514/824; 514/878; 514/879
[58] Field of Search ............... 514/19, 824, 878, 879

[56] References Cited

U.S. PATENT DOCUMENTS

| | | | |
|---|---|---|---|
| 4,720,484 | 1/1988 | Vincent et al. | 514/18 |
| 4,965,250 | 10/1990 | Vincent et al. | 514/18 |
| 5,047,400 | 9/1991 | Vincent et al. | 514/18 |
| 5,098,888 | 3/1992 | Vincent et al. | 514/18 |

*Primary Examiner*—Ronald W. Griffin
*Attorney, Agent, or Firm*—Gordon W. Hueschen

[57] ABSTRACT

The invention relates to compounds of formula (I):

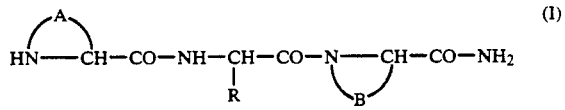

in which:
- A represents, with the carbon and nitrogen atoms to which it is linked, cyclic amide as defined in the description,
- B represents, with the nitrogen and carbon atoms to which it is linked, saturated polycyclic structure as defined in the description,
- R represents hydrogen, optionally substituted lower alkyl, optionally substituted (4-imidazolyl)methyl, (3-pyrazolyl)methyl or optionally substituted (2-pyridyl)methyl, their enantiomers, diastereoisomers and epimers as well as their addition salts with a pharmaceutically acceptable acid.

Medicinal products.

7 Claims, No Drawings

PEPTIDE COMPOUNDS CONTAINING A CYCLIC AMIDE STRUCTURE

The present invention relates to new peptide compounds.

It is now widely recognized that the cholinergic system exerts a major beneficial influence on mnestic phenomena, both of memorization and of recall. Similarly, it is well known that the noradrenergic system is closely involved in the faculties of concentration and attention. These two systems are deficient during cerebral aging, and are very vulnerable during acute or progressive degenerative diseases such as Alzheimer's dementia and stroke.

Moreover, among natural peptides, TRH (thyrotropin-releasing hormone) is capable of facilitating cholinergic neurotransmission, in particular by promoting synthesis of the neuromediator when the latter is rendered deficient or by enhancing the central effect of a cholinergic agonist.

However, exogenously supplied TRH remains relatively inactive as a result of its rapid degradation in the body.

For this reason, tripeptide analogs have been described in order to increase substantially the cholinergic effects of the natural peptide.

This is the case, for example, with the tripeptides described in Patents FR 2,187,155, 2,287,916, 2,266,515 and 2,345,448, in which the pyroglutamyl residue is replaced by another heterocyclic carboxylic acid residue, which possess anticonvulsant and antidepressant properties. Finally, Patent FR 2,585,709 describes peptides in which the prolinamide residue is replaced by a saturated bicyclic structure and which are capable of stimulating cyclic AMP synthesis in cerebral tissue. However, these compounds have practically no activity when administered orally.

The compounds of the present invention have proved to be especially advantageous on account of the intensity of their properties of facilitating cholinergic neurotransmission, since these properties are exerted at doses 50 times lower than those of TRH, administered as a reference compound, and for a much longer period. This intensity of facilitating effect occurs in the same manner with respect to noradrenergic neurotransmission.

Thus, the compounds of the invention can improve mnestic and cognitive performance as a result of simultaneous cholinergic and noradrenergic facilitation. They are hence useful for the treatment of behavioral and constitutional disorders associated with aging and with acute or chronic neuronal degenerative diseases such as, for example, Alzheimer's disease, stroke, spinal trauma or amyotrophic lateral sclerosis.

The invention relates more especially to new compounds containing a cyclic amide structure, corresponding to the general formula (I):

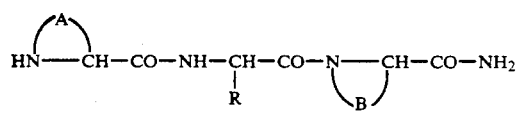

(I)

in which:
A represents, with the nitrogen and carbon atoms to which it is linked:
  a 2-oxoperhydro-7-azepinyl group
  a 2-oxoperhydro-8-azocinyl group
  a 2-oxoperhydro-9-azoninyl group
  a 2-oxoperhydro-10-azecinyl group
  a 2-oxo-2,3,4,7-tetrahydrobenz[e]azepin-7-yl group
  a 2-oxo-2,3,6,7-tetrahydrobenz[d]azepin-7-yl group
  a 2-oxo-2,5,6,7-tetrahydrobenz[c]azepin-7-yl group
B represents, with the nitrogen and carbon atoms to which it is linked, a polycyclic structure selected from the following structures:
  2-azabicyclo[2.2.1]heptane,
  2-azabicyclo[2.2.2]octane, optionally substituted at positions 1 and 4 with one or two linear or branched ($C_1$-$C_4$) alkyl groups,
  perhydroindole,
  perhydroisoindole,
  indoline,
  isoindoline,
  perhydroquinoline,
  perhydroisoquinoline,
  1,2,3,4-tetrahydroquinoline,
  1,2,3,4-tetrahydroisoquinoline,
  cyclopenta[b]pyrrolidine,
  pyrrolidine, optionally substituted with one or two linear or branched ($C_1$-$C_4$) alkyl groups,
  piperidine,
  thiazolidine,
R represents:
  a hydrogen atom,
  a linear or branched ($C_1$-$C_6$) alkyl group optionally substituted with an amino group or a guanidino group,
  a (4-imidazolyl)methyl group optionally substituted on one of the nitrogen atoms with a linear or branched ($C_1$-$C_4$) alkyl radical,
  a (3-pyrazolyl)methyl group,
  a (2-pyridyl)methyl group optionally substituted with an amino group,
their enantiomers, diastereoisomers and epimers, as well as their addition salts with a pharmaceutically acceptable acid.

Among the pharmaceutically acceptable acids, hydrochloric, sulfuric, tartaric, maleic, fumaric, oxalic, methanesulfonic and camphoric acids, and the like, may be mentioned without implied limitation.

The invention also encompasses the process for preparing the compounds of the formula (I), wherein the amine function of an amino acid of formula (II), the isomers of which have optionally been separated by a conventional separating technique:

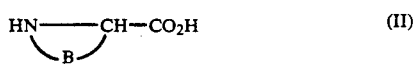

(II)

in which B has the same meaning as in the formula (I), is protected with a protective radical (P) such as tert-butoxycarbonyl (tBOC) or benzyloxycarbonyl (Z), through the action of a suitable reagent, to lead to a compound of formula (III):

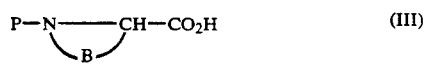

(III)

in which B and P have the same meaning as above, which is reacted, at a temperature of between $-15°$ and $0°$ C., in the presence of triethylamine, with ethyl chloroformate and then ammonia solution, to lead to a compound of formula (IV):

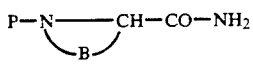  (IV)

in which B and P have the same meaning as above, which is deprotected by a suitable process such as, for example, the action of gaseous hydrochloric acid in an anhydrous solvent such as dioxane or ethyl acetate the case where P=tBOC or by catalytic hydrogenation in the case where P=Z, to lead to a compound of formula (V):

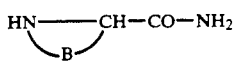  (V)

in which B has the same meaning as in the formula (I), the isomers of which are separated, if so desired, by a conventional separating technique, which is coupled with a second protected amino acid of formula (VI) according to the peptide coupling technique described by W. KONIG and R. GEIGER (Ber. 103, 788, 1970):

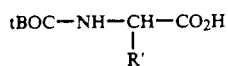  (VI)

in which R' represents a hydrogen atom, a linear or branched ($C_1$-$C_6$) alkyl group optionally substituted with an amino group protected, for example, by a benzyloxycarbonyl radical (Z) or a guanidino group itself protected, for example, by a nitro radical, a (4-imidazolyl)methyl group optionally substituted on one of the nitrogen atoms with a linear or branched ($C_1$-$C_4$) alkyl radical, a (3-pyrazolyl)methyl group or a (2-pyridyl)methyl group optionally substituted with an amino group protected, for example, by a benzyloxycarbonyl radical, to lead to a compound of formula (VII):

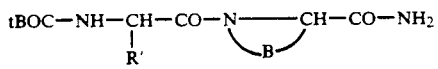  (VII)

which R' and B have the same meaning as above, the diastereoisomers or enantiomers of which are separated, if so desired, by a conventional separating technique, which is then deprotected by the action of gaseous hydrochloric acid in an anhydrous solvent such as, for example, dioxane or ethyl acetate, to lead to a compound of formula (VIII):

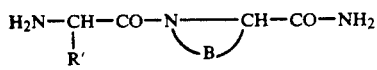  (VIII)

in which R' and B have the same meaning as above, which is coupled with a third amino acid of formula (IX) according to the peptide coupling technique described by G. ANDERSON and J. ZIMMERMAN (J.A.C.S., 85, 3039, 1963):

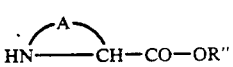  (IX)

which R'' is a succinimide radical, to lead:
either:
to a compound of formula (I) in the case where R' is other than a linear or branched ($C_1$-$C_6$) alkyl group substituted with a protected amino or protected guanidino group, or other than a (2-pyridyl)methyl group substituted with a protected amino group, the isomers of which are separated, if so desired, according to a conventional separating technique and which is then, if necessary, converted to an addition salt with a pharmaceutically acceptable acid,
or:
to a compound of formula (X):

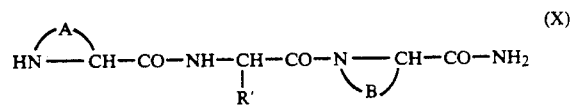  (X)

in the case where A and B have the same meaning as in the formula (I) and R' is a linear or branched ($C_1$-$C_6$) alkyl group substituted with a protected amino or protected guanidino group or R' is a (2-pyridyl)methyl group substituted with a protected amino group, the isomers of which are separated, if so desired, according to a conventional separating technique and which is deprotected by catalytic hydrogenation, for example, to lead to a compound of formula (I), the isomers of which are separated, where appropriate, according to a conventional separating technique and which is then, if necessary, converted to an addition salt with a pharmaceutically acceptable acid.

The compounds of formula (I) possess advantageous pharmacological properties, which are manifested with very much greater intensity and at much lower doses than those of the compounds of the prior art.

Thus, at doses of 0.1 to 0.3 mg/kg upwards, the compounds of the invention facilitate central cholinergic neurotransmission, on the one hand restoring high-affinity choline uptake, a limiting parameter in the synthesis of acetylcholine when the latter is rendered experimentally deficient, and on the other hand enhancing the central cholinergic effects of a muscarinic agonist.

At the same low doses, these compounds facilitate central noradrenergic neurotransmission, countering the loss of righting reflexes and capacities for vigilance induced by an $a_2$ agonist, xylazine.

This dual facilitation enables the compounds of the invention to promote at low dose the mnestic capacities and the faculties of attention and motivation.

The subject of the present invention is also pharmaceutical compositions containing as active principle at least one compound of general formula (I) or one of its addition salts with a pharmacologically acceptable acid, alone or in combination with one or more non-toxic, inert excipients or vehicles.

Among the pharmaceutical compositions according to the invention, those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like, may be mentioned more especially.

The appropriate dosage varies according to the patient's age and weight and the nature and severity of the condition, as well as the administration route.

The latter can be oral, nasal, rectal or parenteral. Generally speaking, single doses range between 0.05 and 300 mg for a treatment administered in 1 or 3 doses per 24 hours. The examples which follow illustrate the invention and in no way limit the latter.

The abbreviations used in the examples are as follows:

AZEP in place of 2-oxoperhydro-7-azepinecarbonyl,
AZOC in place of 2-oxoperhydro-8-azocinecarbonyl,
AZON in place of 2-oxoperhydro-9-azoninecarbonyl,
AZEC in place of 2-oxoperhydro-10-azecinecarbonyl,
3-oxoBzAZEP in place of 3-oxo-2,3,4,5-tetrahydro-1H-2-benzazepine-1-carbonyl, the structural formula of which is as follows:

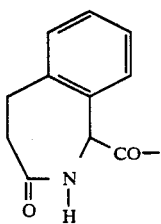

1-oxoBzAZEP in place of 1-oxo-2,3,4,5-tetrahydro-1H-2-benzazepine-3-carbonyl, the structural formula of which is as follows:

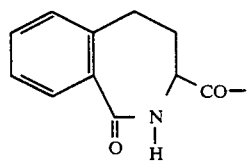

2-oxoBzAZEP in place of 2-oxo-2,3,4,5-tetrahydro-1H-3-benzazepine-4-carbonyl, the structural formula of which is as follows:

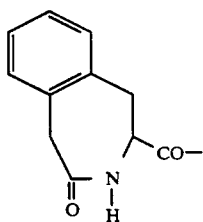

($N^l$-Me)His in place of 1-methylhistidyl, the structural formula of which is as follows:

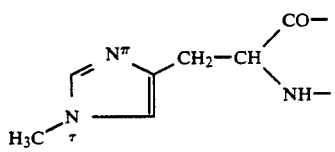

($N^\pi$-Me)His in place of 3-methylhistidyl, the structural formula of which is as follows:

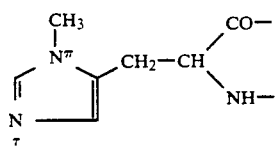

His in place of histidyl,
Leu in place of leucyl,
Lys in place of lysyl,
Arg in place of arginyl,
Gly in place of glycyl,
Pyra in place of (3-pyrazolyl)alanyl,
AmPyri in place of (4-amino-2-pyridyl)alanyl,
ABH in place of 2-aza-3-carbonylbicyclo[2.2.1]heptane,
Pro in place of prolyl,
BOC in place of butoxycarbonyl,
Z in place of benzyloxycarbonyl,
ABO in place of 2-azabicyclo[2.2.2]octane-3-carbonyl,
PHI in place of perhydro-2-indolecarbonyl,
THIQ in place of 1,2,3,4-tetrahydro-3-isoquinoline carbonyl,
ThiaPro in place of 4-thiaprolyl,
Lys/$\tau$ in place of N$\tau$-benzyloxycarbonyllysyl,
Arg/NO2 in place of N-nitroarginyl.

EXAMPLE 1:
AZEP-(S)(N$\tau$-Me)His-(1S,3S,4R)ABH-NH$_2$ "isomer A"

Stage A: N-Hydroxysuccinimide activated ester of (RS)AZEP-OH 20 mmol of AZEP-OH, obtained by saponification according to the method described by E. PERROTI et al. (Ann. Chim., Rome, 56, (11), 1358, 1966) of the corresponding ethyl ester, itself obtained according to the method described by C. J. LU and F. F. BLICKE (C.A. 52, 11086f), are placed in a 500-cm$^3$ three-necked flask equipped with a thermometer and a calcium chloride guard tube and containing 150 cm$^3$ of anhydrous tetrahydrofuran. The mixture is cooled in ice-cold water. 20 mmol of N-hydroxysuccinimide dissolved in 100 cm$^3$ of anhydrous tetrahydrofuran are then added with stirring, followed by 20 mmol of dicyclohexylcarbodiimide. Stirring is maintained for 18 hours, allowing the mixture to return to room temperature. After the dicyclohexylurea formed is filtered off, the expected product is obtained by evaporation of the filtrate. Yield: 99%

Stage B: (RS)AZEP-(S)(N$\tau$-Me)His-(1S,3S,4R)ABH-NH$_2$

Using the peptide coupling method described by G. W. ANDERSON and J. E. ZIMMERMAN (J.A.C.S., 85, 3039, 1963), 20 mmol of (S)(N$\tau$-Me)His-(1S,3S,4R)ABH-NH$_2$ dihydrochloride, described in French Patent Application 89/08,672, are reacted with 20 mmol of the compound obtained in Stage A.

After conventional treatment and purification by chromatography on silica gel, using a dichloromethane/methanol/ammonia solution mixture in the proportions 90:10:1 as eluent, the expected product is obtained. Yield: 78%

Stage C: AZEP-(S)(Nτ-Me)His-(1S,3S,4R)ABH-NH₂ "isomer A"

The mixture of isomers obtained in the preceding stage is separated by preparative HPLC on a Lichroprep RP-18 column, using a water/acetonitrile/acetic acid mixture in the proportions 97.5:2.5:0.1 as eluent. The isomers, designated "A" and "B" in order of emergence from the column, are obtained in the form of acetates, which are converted to their bases by passage through Amberlite IRA 93 resin followed by evaporation and lyophilization. The isomeric purity of the expected product is verified by HPLC. Optical rotation: $[\alpha]_D^{20} = -26.8°$ (c=2%, ethanol)

|  | Elemental microanalysis: | | |
| --- | --- | --- | --- |
|  | C % | H % | N % |
| Calculated | 58.59 | 7.02 | 19.52 |
| Found | 58.31 | 7.43 | 19.49 |

EXAMPLE 2: AZEP-(S)(Nτ-Me)His-(1S,3S,4R)ABH-NH₂ "isomer B"

Stages A, B, and C are identical to those of Example 1. The "B" isomer is obtained in stage C, after elution of the "A" isomer of Example 1.

Proton Nuclear Magnetic Resonance (D₂O)

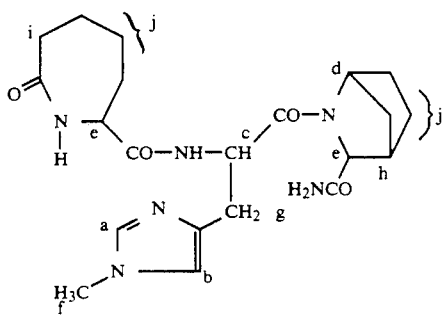

a δ = 7.5 ppm (1H, s)
b δ = 7.0 ppm (1H, s)
c δ = 5.0 ppm (1H, m)
d δ = 4.6 ppm (1H, m)
e δ = 4.2 ppm (2H, m)
f δ = 3.6 ppm (3H, s)
g δ = 3.0 ppm (2H, d)
h δ = 2.8 ppm (1H, m)
i δ = 2.4 ppm (2H, m)
j δ = 1.7 ppm (12H, m)

EXAMPLE 3: AZOC-(S)(Nτ-Me)His-(1S,3S,4R)ABH-NH₂ "isomer A"

Stage A: N-Hydroxysuccinimide activated ester of (RS)AZOC-OH

Using the procedure described in Stage A of Example 1, but replacing the ethyl ester of AZEP-OH by the ethyl ester of AZOC-OH, obtained according to the method described by C. J. LU and F. F. BLICKE (C.A. 52, 11086f), the expected product is obtained. Yield: 99%

Stage B: (RS)AZOC-(S)(Nτ-Me)His (1S,3S,4R)ABH-NH₂

Using the procedure described in Stage B of Example 1, but replacing the activated ester of (RS)AZEP-OH by the activated ester of (RS)AZOC-OH obtained in the preceding stage, the expected product is obtained. Yield: 63%

Stage C: AZOC-(S)(Nτ-Me)His-(1S,3S,4R)ABH-NH₂ "isomer A"

The method of separation and purification of the isomers is the same as that employed in Stage C of Example 1, it being understood that the "A" and "B" isomers are so named in order of emergence from the column.

|  | Elemental microanalysis: | | |
| --- | --- | --- | --- |
|  | C % | H % | N % |
| Calculated | 59.44 | 7.26 | 18.91 |
| Found | 59.38 | 7.39 | 18.72 |

EXAMPLE 4: AZOC (S)(Nτ-Me)His-(1S,3S,4R)ABH-NH₂ "isomer B"

Stages A, B and C are identical to those of Example 3. The method of purification of the "B" isomer, obtained after elution of the "A" isomer, is the same as that used for the "A" isomer of Example 3.

Proton Nuclear Magnetic Resonance (CDCl₃):

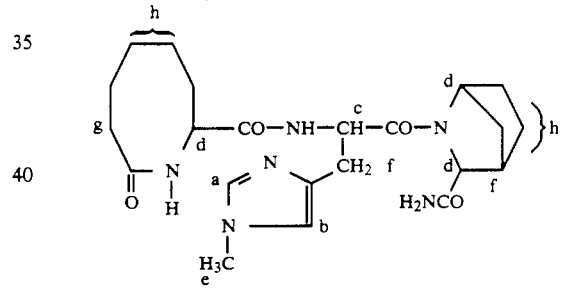

a δ = 7,27 ppm (1H, s)
b δ = 6,65 ppm (1H, s)
c δ = 4,90 ppm (1H, m)
d δ entre 4,6 et 4,0 ppm (3H, m)
e δ = 3,63 ppm (3H, s)
f δ entre 3,22 et 2,85 ppm (3H, m)
g δ entre 2,45 et 2,20 ppm (2H, m)
h δ entre 2,0 et 1,2 ppm (14H, m)

EXAMPLE 5: (S)AZEP-(S)His-(S)Pro-NH₂

Stage A: (RS)AZEP (S)His-(S)Pro NH₂

Using the procedure described in Stage B of Example 1 but replacing (S)(Nτ-Me)His-(1S,3S,4R)ABH-NH₂ dihydrochloride by (S)His-(S)Pro-NH₂ dihydrochloride, the expected product is obtained. Yield: 68%

Stage B: (S)AZEP-(S)His-(S)Pro-NH₂

The method of separation and purification of the isomers is the same as that employed in Stage C of Example 1. The elution solvent used is a water/acetic acid mixture in the proportions 99.8:0.2. The compound of Example 5 is the first one to emerge from the column. Optical rotation: $[\alpha]_D^{20} = -36.4°$ (c=1%, ethanol)

Proton Nuclear Magnetic Resonance (CDCl₃):

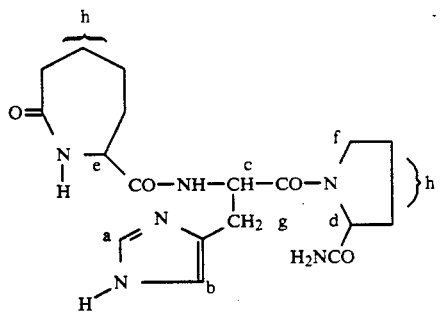

a δ = 7.5 ppm (1H, s)
b δ = 6.9 ppm (1H, s)
c δ = 4.6 ppm (1H, m)
d δ = 4.25 ppm (1H, m)
e δ = 4.05 ppm (1H, m)
f δ between 3.6 and 3.2 ppm (2H, m)
g δ between 3.1 and 2.4 ppm (2H, m)
h δ between 2.4 and 1.2 ppm (12H, m)

EXAMPLE 5a: (S)AZEP-(S)His-(S)Pro-NH₂

Stage A: (S)AZEP-OH

The expected product is obtained after derivatization of (RS)AZEP-OH with (S)(−)-α-methylbenzylamine, recrystallizations of the derivative in an ethyl acetate/methanol (90:10) mixture and then hydrolysis.

The optical rotation of the 2-aminopimelic acid obtained after 5 hours of refluxing of the derivatization product in a concentrated hydrochloric acid medium is compared with that of the 2-aminopimelic acid of known configuration described by R. WADE et al. (J.A.C.S., 79, 648-652, 1957). Optical rotation of (S)-2-aminopimelic acid: $[\alpha]_D^{20} = +21.5°$ (c=1%, 5N HCl)

This enables it to be deduced that the AZEP-OH isomer obtained is of the S configuration. Optical rotation: $[\alpha]_D^{20} = +9.24°$ (c=1%, ethanol)

Stage B: (S)AZEP-(S)His-(S)Pro-NH₂

The expected product is obtained as in Stage A of Example 5, but replacing (RS)AZEP-OH by (S)AZEP-OH obtained in the preceding stage.

The physicochemical characteristics are those of the compound of Example 5.

EXAMPLE 6: (R)AZEP-(S)His-(S)Pro-NH₂

Stages A and B are identical to those of Example 5. The compound of Example 6 is obtained after elution of the compound of Example 5.

Proton Nuclear Magnetic Resonance (CDCl₃):

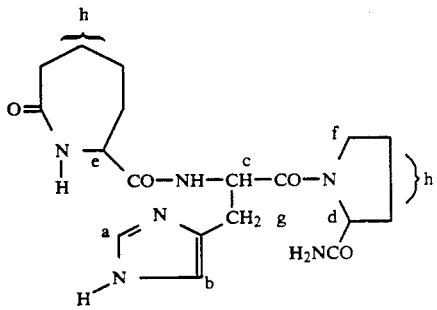

a δ = 7.5 ppm (1H, s)
b δ = 6.9 ppm (1H, s)
c δ = 4.6 ppm (1H, m)
d δ = 4.25 ppm (1H, m)
e δ = 4.05 ppm (1H, m)
f δ between 3.6 and 3.2 ppm (2H, m)
g δ between 3.1 and 2.4 ppm (2H, m)
h δ between 2.4 and 1.2 ppm (12H, m)

EXAMPLE 7: AZEP-(S)His-(1S,3S,4R)ABH-NH₂ "isomer A"

Stage A: (RS)AZEP-(S)His-(1S,3S,4R)ABH-NH₂

Using the procedure described in Stage B of Example 1, but replacing (S)(Nτ-Me)His-(1S,3S,4R)ABH-NH₂ dihydrochloride by (S)His-(1S,3S,4R)ABH-NH₂ dihydrochloride described in French Patent Application 89/08,672, the expected product is obtained.

The elution solvent used for separation of the isomers is a water/acetic acid mixture in the proportions 99.8:0.2. Yield: 64%

Proton Nuclear Magnetic Resonance (CDCl₃):

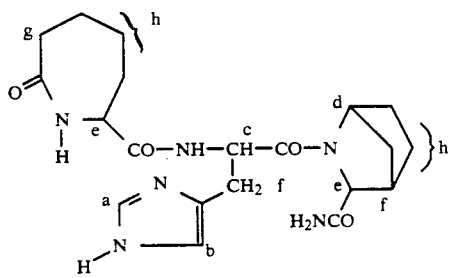

a δ = 7.55 ppm (1H, s)
b δ = 6.85 ppm (1H, s)
c δ = 4.8 ppm (1H, m)
d δ = 4.55 ppm (1H, m)
e δ between 4.1 and 3.9 ppm (2H, m)
f δ between 3.1 and 2.6 ppm (3H, m)
g δ between 2.4 and 2.1 ppm (2H, m)
h δ between 1.9 and 1.2 ppm (12H, m)

EXAMPLE 8: AZEP-(S)His-(1S,3S,4R)ABH-NH₂ "isomer B"

Stages A and B are identical to those of Example 7. The "B" isomer is obtained after elution of the "A" isomer of Example 7.

| | Elemental microanalysis: | | |
| --- | --- | --- | --- |
| | C % | H % | N % |
| Calculated | 57.68 | 6.78 | 20.18 |
| Found | 57.99 | 6.57 | 20.40 |

EXAMPLE 9: AZOC-(S)His-(S)Pro-NH₂ "isomer A"

Using the procedure described in Stage B of Example 3, but replacing (S)(Nτ-Me)His-(1S,3S,4R)ABH-NH₂ dihycrochloride by (S)His-(S)Pro-NH₂ dihydrochloride, the expected product is obtained.

The elution solvent used for separation of the isomers is a water/acetic acid mixture in the proportions 99.8:0.2.

Proton Nuclear Magnetic Resonance (DMSO-d$_6$):

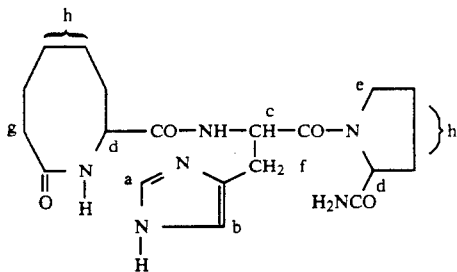

a δ = 7,55 ppm (1H, s)
b δ = 6,9 ppm (1H, s)
c δ = 4,6 ppm (1H, m)
d δ entre 4,4 et 4,1 ppm (2H, m)
e δ entre 3,5 et 3,2 ppm (2H, m)
f δ = 2,9 ppm (2H, m)
g δ = 2,05 ppm (2H, m)
h δ entre 1,9 et 1,1 ppm (12H, m)

EXAMPLE 10: AZOC-(S)His-(S)Pro-NH$_2$ "isomer B"

The "B" isomer is obtained after elution of the "A" isomer of Example 9.

Proton Nuclear Magnetic Resonance (DMSO-d$_6$):

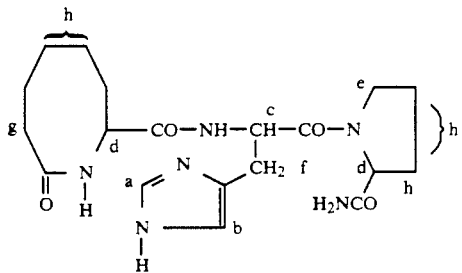

a δ = 7.55 ppm (1H, s)
b δ = 6.9 ppm (1H, s)
c δ = 4.6 ppm (1H, m)
d δ between 4.4 and 4.1 ppm (2H, m)
e δ between 3.5 and 3.2 ppm (2H, m)
f δ = 2.9 ppm (2H, m)
g δ = 2.05 ppm (2H, m)
h δ between 1.9 and 1.1 ppm (12H, m)

EXAMPLE 11: AZOC-(S)His-(1S,3S,4R)ABH-NH$_2$ "isomer A"

Using the procedure described in Example 3, but replacing (S)(Nτ-Me)His-(1S,3S,4R)ABH-NH$_2$ dihydrochloride in Stage B by (S)His-(1S,3S,4R)ABH-NH$_2$ dihydrochloride, the expected product is obtained. The elution solvent used for separation of the isomers is a water/acetic acid mixture in the proportions 99.8:0.2.

Proton Nuclear Magnetic Resonance (DMSO-d$_6$):
aδ = 7.5 ppm (1H,s)
fδ = 4.05 ppm (1H,m)  bδ = 6.9 ppm (1H,s)
gδ between 3.1 and 2.8 ppm  cδ = 4.8 ppm (1H,m)
(2H,m)  dδ = 4.5 ppm (1H,m)
hδ = 2.7 ppm (1H,m)  eδ = 4.3 ppm (1H,m)
iδ between 2.45 and 2.1 ppm (2H,m)
jδ between 1.9 and 1.1 ppm (14H,m)

EXAMPLE 12: AZOC-(S)His-(1S,3S,4R)ABH-NH$_2$ "isomer B"

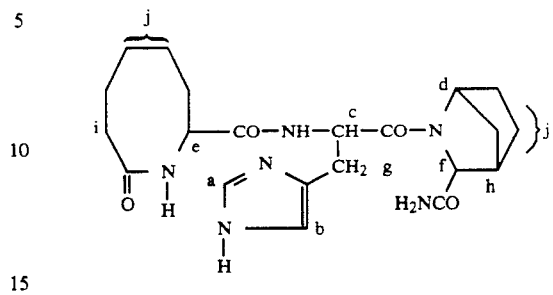

The "B" isomer is obtained after elution of the "A" isomer of Example 11.

Proton Nuclear Magnetic Resonance (DMSO-d$_6$):

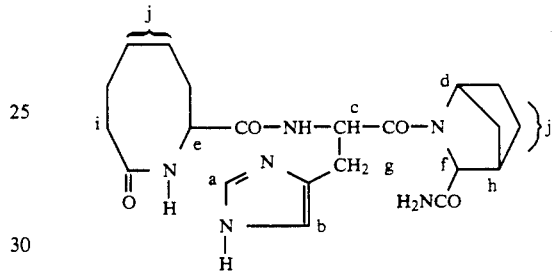

a δ = 7.45 ppm (1H, s)
b δ = 6.8 ppm (1H, s)
c δ = 4.8 ppm (1H, m)
d δ = 4.5 ppm (1H, m)
e δ = 4.3 ppm (1H, m)
f δ = 4.00 ppm (1H, m)
g δ between 3.1 and 2.7 ppm (2H, m)
h δ = 2.65 ppm (1H, m)
i δ between 2.45 and 2.1 ppm (2H, m)
j δ between 1.8 and 1.1 ppm (14H, m)

EXAMPLE 13: AZEP-(S)(Nτ-Me)His-(S)Pro-NH$_2$ "isomer A"

Using the procedure described in Example 1, but replacing (S)(Nτ-Me)His-(1S,3S,4R)ABH-NH$_2$ dihydrochloride in stage B by (S)(Nτ-Me)His-(S)Pro-NH$_2$ dihydrochloride, the expected product is obtained. (Elution solvent:water/acetic acid, 99.8:0.2)

Proton Nuclear Magnetic Resonance (DMSO-d$_6$):

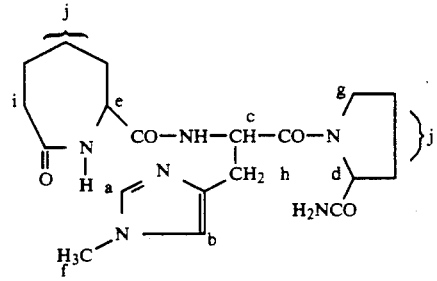

a δ = 7.5 ppm (1H, s)
b δ = 6.9 ppm (1H, s)
c δ between 4.7 and 4.5 ppm (1H, m)
d δ between 4.25 and 4.1 ppm (1H, m)
e δ between 4.1 and 3.9 ppm (1H, m)
f δ = 3.6 ppm (3H, s)

-continued
g δ between 3.5 and 3.2 ppm (2H, m)
h δ between 3.0 and 2.7 ppm (2H, m)
i δ between 2.45 and 2.1 ppm (2H, m)
j δ between 2.1 and 1.3 ppm (10H, m)

EXAMPLE 14: AZEP-(S)(Nτ-Me)His-(S)Pro-NH$_2$ "isomer B"

The "B" isomer is obtained after elution of the "A" isomer of Example 13.

Proton Nuclear Magnetic Resonance (DMSO-d$_6$):

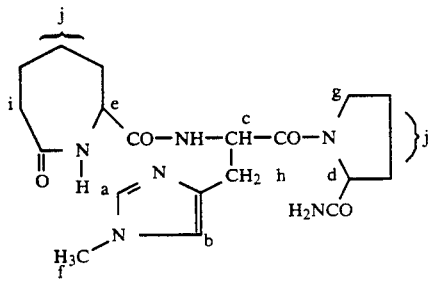

a δ = 7.5 ppm (1H, s)
b δ = 6.9 ppm (1H, s)
c δ between 4.8 and 4.5 ppm (1H, m)
d δ between 4.30 and 4.15 ppm (1H, m)
e δ0 between 4.0 and 3.9 ppm (1H, m)
f δ = 3.6 ppm (3H, m)
g δ between 3.4 and 3.2 ppm (2H, m)
h δ between 3.0 and 2.6 ppm (2H, m)
i δ between 2.40 and 2.2 ppm (2H, m)
j δ between 2.1 and 1.3 ppm (10H, m)

EXAMPLE 15: AZEP-(S)(Nτ-Me)His-(S)Pro-NH$_2$ "isomer A"

Using the procedure described in Example 1, but replacing the (S)(Nτ-Me)His-(1S,3S,4R)ABH-NH$_2$ dihydrochloride, the in Stage B by (S)(Nτ-Me)His-(S)Pro-NH$_2$ dihydrochloride, the expected product is obtained. Yield: 84%

Proton Nuclear Magnetic Resonance (DMSO-d$_6$):

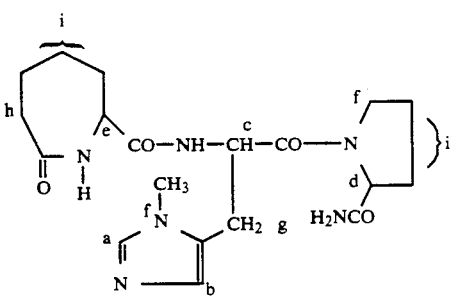

a δ = 7.5 ppm (1H, s)
b δ = 6.5 ppm (1H, s)
c δ = 4.85 ppm (1H, m)
d δ = 4.25 ppm (1H, m)
e δ = 3.95 ppm (1H, m)
f δ = 3.6 ppm (5H, m)
g δ between 3.0 and 2.6 ppm (2H, m)
h δ = 2.3 ppm (2H, m)
i δ between 1.9 and 1.2 ppm (10H, m)

EXAMPLE 16: AZEP-(S)(Nτ-Me)His-(S)Pro-NH$_2$ "isomer B"

The "B" isomer is obtained after elution of the "A" isomer of Example 15.

Proton Nuclear Magnetic Resonance (DMSO-d$_6$):

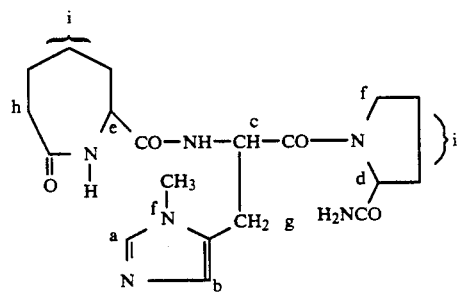

a δ = 7.5 ppm (1H, s)
b δ = 6.5 ppm (1H, s)
c δ = 4.85 ppm (1H, m)
d δ = 4.25 ppm (1H, m)
e δ = 3.95 ppm (1H, m)
f δ = 3.6 ppm (5H, m)
g δ between 3.0 and 2.6 ppm (2H, m)
h δ = 2.3 ppm (2H, m)
i δ between 1.9 and 1.2 ppm (10H, m)

EXAMPLE 17: AZEP-(S)Leu-(1S,3S,4R)ABH-NH$_2$ "isomer A"

Using the procedure described in Example 1, but replacing (S)(Nτ-Me)His-(1S,3S,4R)ABH-NH$_2$ dihydrochloride in Stage B by (S)Leu-(1S,3S,4R)ABH-NH$_2$ hydrochloride described in French Patent Application 89/08,672, the expected product is obtained.

The elution solvent used for separation of the isomers is a dichloromethane/methanol/ammonia solution mixture in the proportions 90:10:0.5.

| | Elemental microanalysis: | | |
|---|---|---|---|
| | C % | H % | N % |
| Calculated | 61.20 | 8.22 | 14.27 |
| Found | 61.66 | 7.99 | 14.14 |

EXAMPLE 18: AZEP-(S)Leu-(1S,3S,4R)ABH-NH$_2$ "isomer B"

The "B" isomer is obtained after elution of the "A" isomer of Example 17.

| | Elemental microanalysis: | | |
|---|---|---|---|
| | C % | H % | N % |
| Calculated | 61.20 | 8.22 | 14.27 |
| Found | 61.39 | 8.01 | 14.30 |

EXAMPLE 19: AZEP-(S)Leu-(S)Pro-NH$_2$ "isomer A"

Using the procedure described in Example 1, but replacing (S)(Nτ-Me)His-(1S,3S,4R)ABH-NH$_2$ dihydrochloride by (S)Leu-(S)Pro-NH$_2$ hydrochloride, the expected product is obtained.

The elution solvent used for separation of the isomers is a dichloromethane/methanol/ammonia solution mixture in the proportions 90:10:0.5.

| Elemental microanalysis: | | | |
|---|---|---|---|
| | C % | H % | N % |
| Calculated | 59.00 | 8.25 | 15.29 |
| Found | 59.14 | 8.50 | 15.11 |

EXAMPLE 20: AZEP-(S)Leu-(S)Pro-$NH_2$ "isomer"

The "B" isomer is obtained after elution of the "A" isomer of Example 19.

| Elemental microanalysis: | | | |
|---|---|---|---|
| | C % | H % | N % |
| Calculated | 59.00 | 8.25 | 15.29 |
| Found | 59.33 | 8.35 | 14.79 |

EXAMPLE 21: AZEP-(S)Lys-(S)Pro-$NH_2$ "isomer A"

Stage A: AZEP-(S)Lys/z-(S)Pro-$NH_2$ "isomer A"

Using the procedure described in Stage B of Example 1, but replacing (S)(Nτ-Me)His-(1S,3S,4R)ABH-$NH_2$ dihydrochloride by (S)Lys/z-(S)Pro-$NH_2$ trifluoroacetate, the expected product is obtained.

The elution solvent used for separation of the isomers is a dichloromethane/methanol/ammonia solution mixture in the proportions 90:10:0.5. Yield: 77%

Stage B: AZEP-(S)Lys-(S)Pro-$NH_2$ "isomer A"

Deprotection of the compound obtained in Stage A is carried out by hydrogenolysis in ethanol in the presence of palladinized charcoal. After the catalyst is filtered off and the ethanol evaporated off, the expected product is obtained by dissolution in water followed by lyophilization.

| Elemental microanalysis: | | | |
|---|---|---|---|
| | C % | H % | N % |
| Calculated | 56.67 | 8.19 | 18.36 |
| Found | 56.26 | 7.89 | 17.95 |

EXAMPLE 22: AZEP-(S)Lys-(S)Pro-$NH_2$ "isomer B"

The "B" isomer is obtained after elution of the "A" isomer of Example 21.

| Elemental microanalysis: | | | |
|---|---|---|---|
| | C % | H % | N % |
| Calculated | 56.67 | 8.19 | 18.36 |
| Found | 56.12 | 8.27 | 17.90 |

EXAMPLE 23: AZEP-(S)Lys-(1S,3S,4R)ABH-$NH_2$ "isomer A"

Stage A: BOC(S)Lys/$_z$-(1S,3S,4R)ABH-$NH_2$

Using the peptide coupling technique described by W. KONIG and R. GEIGER (Ber, 103, 788, 1970) and dimethylformamide as a solvent, the expected product is obtained from BOC(S)Lys/$_z$ and (1S,3S,4R)ABH-$NH_2$ after purification on silica gel (elution solvent:dichloromethane/methanol, 97:3) Yield: 84%

Stage B: (S)Lys/$_z$-(1S,3S,4R)ABH-$NH_2$ hydrochloride

The compound obtained in Stage A is deprotected in 4N hydrochloric acid in ethyl acetate for 1 hour at 0° C. and then 18 hours at room temperature.

The expected product is obtained by filtering off the precipitate, washing with ether and then drying. Yield: 90%

Stage C: AZEP-(S)Lys/$_z$(1S,3S,4R)ABH-$NH_2$ "isomer A"

Using the procedure described in Stage A of Example 21, but replacing (S)Lys/$_z$-(S)Pro-$NH_2$ trifluoroacetate by (S)Lys/$_z$-(1S,3S,4R)ABH-$NH_2$ hydrochloride obtained in the preceding stage, the expected product is obtained.

Stage D: AZEP-(S)Lys-(1S,3S,4R)ABH-$NH_2$ "isomer A"

The method of deprotection is the same as that used in Stage B of Example 21.

Proton Nuclear Magnetic Resonance (DMSO-$d_6$):

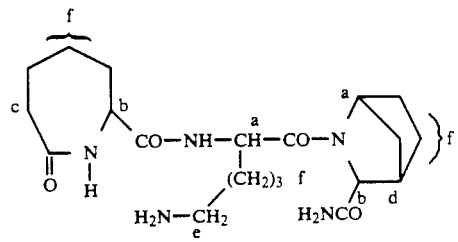

a δ between 4.6 and 4.4 ppm (2H, m)
b δ between 4.2 and 4.1 ppm (2H, m)
c δ between 3.0 and 2.5 ppm (2H, m)
d δ = 2.6 ppm (1H, m)
e δ between 2.4 and 2.2 ppm (2H, m)
f δ between 2.0 and 1.2 ppm (18H, m)

EXAMPLE 24: AZEP (S)Lys-(1S,3S,4R)ABH-$NH_2$ "isomer B"

The "B" isomer is obtained after deprotection of the "B" isomer eluted after the "A" isomer in Stage C of Example 23.

Proton Nuclear Magnetic Resonance (DMSO-$d_6$):

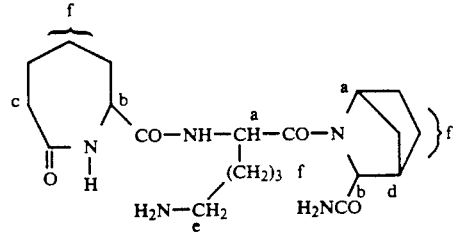

a δ between 4.6 and 4.4 ppm (2H, m)
b δ between 4.2 and 4.1 ppm (2H, m)
c δ between 3.0 and 2.5 ppm (2H, m)
d δ = 2.6 ppm (1H, m)
e δ between 2.4 and 2.2 ppm (2H, m)
f δ between 2.0 and 1.2 ppm (18H, m)

EXAMPLE 25: AZEP-(S)Arg-(1S,3S,4R)ABH-NH$_2$ "isomer A"

Using the procedure described in Example 23, but replacing BOC(S)Lys/$_z$ in Stage A by BOC(S)Arg-/NO$_2$, and performing the deprotection of the arginyl group before separation of the "A" and "A" isomers, the expected product is obtained. The solvent used for separation of the isomers is an acetic acid/water (2:1000) mixture.

Proton Nuclear Magnetic Resonance (DMSO-d$_6$):

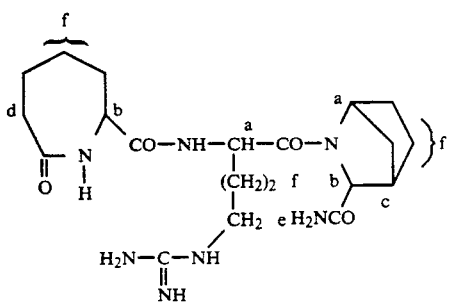

a δ between 4.6 and 4.4 ppm (2H, m)
b δ between 4.15 and 4.00 ppm (2H, m)
c δ = 2.65 ppm (1H, m)
d δ = 3.05 ppm (2H, m)
e δ between 2.5 and 2.1 ppm (2H, m)
f δ between 2.0 and 1.3 ppm (16H, m)

EXAMPLE 26: AZEP-(S)Arg-(1S,3S,4R)ABH-NH$_2$ "isomer B"

The "B" isomer is obtained after elution of the "A" isomer of Example 25.

Proton Nuclear Magnetic Resonance (DMSO-d$_6$):

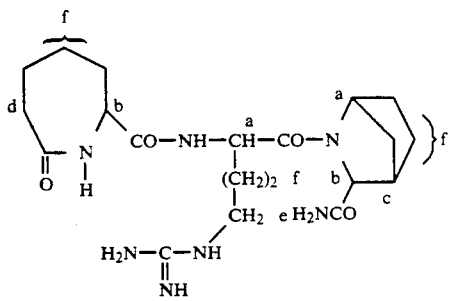

a δ between 4.6 and 4.4 ppm (2H, m)
b δ between 4.15 and 4.00 ppm (2H, m)
c δ = 2.65 ppm (1H, m)
d δ = 3.05 ppm (2H, m)
e δ between 2.5 and 2.1 ppm (2H, m)
f δ between 2.0 and 1.3 ppm (16H, m)

EXAMPLE 27: AZEP-Gly-(1S,3S,4R)ABH-NH$_2$ "isomer A"

Using the procedure described in Example 23 (Stages A, B, C), but replacing BOC(S)Lys/$_z$ in Stage A by BOC-Gly, the expected product is obtained. The solvent used for separation of the isomers is a water/acetonitrile/diethylamine (97:3:0.05) mixture.

Proton Nuclear Magnetic Resonance (DMSO-d$_6$):

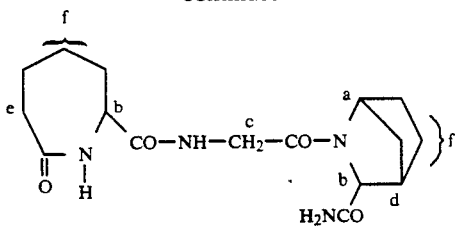

a δ = 4.35 ppm (1H, m)
b δ between 4.2 and 4.1 ppm (2H, m)
c δ between 4.2 and 3.9 ppm (2H, AB syst.)
d δ between 2.8 and 2.6 ppm (1H, m)
e δ between 2.5 and 2.2 ppm (2H, m)
f δ between 2.0 and 1.0 ppm (12H, m)

EXAMPLE 28: AZEP-Gly-(1S,3S,4R)ABH-NH$_2$ "isomer B"

The "B" isomer is obtained after elution of the "A" isomer of Example 27.

Proton Nuclear Magnetic Resonance (DMSO-d$_6$):

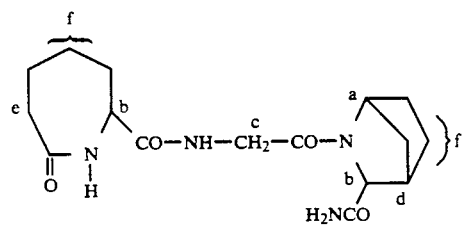

a δ = 4.35 ppm (1H, m)
b δ between 4.2 and 4.1 ppm (2H, m)
c δ between 4.2 and 3.9 ppm (2H, AB syst.)
d δ between 2.8 and 2.6 ppm (1H, m)
e δ between 2.5 and 2.2 ppm (2H, m)
f δ between 2.0 and 1.0 ppm (12H, m)

EXAMPLE 29: 3-oxoBzAZEP-(S)(Nτ-Me)His-(1S,3S,4R)ABH-NH$_2$ "isomer A"0

Using the procedure described in Example 1, but replacing the ethyl ester of (RS)AZEP-OH in Stage A by the methyl ester of (RS)-3-oxoBzAZEP-OH obtained according to the method described in Stage A from 1-(methoxycarbonyl)-β-tetralone described by M. PLIENINGER et al. (Chem. Ber. 108, 3286, 1975), the expected product is obtained.

Proton Nuclear Magnetic Resonance (CDCl$_3$):

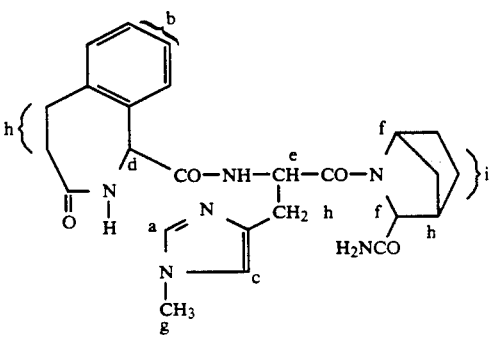

a δ = 7.4 ppm (1H, s)

-continued b δ = 7.2 ppm (4H, m)
c δ = 6.85 ppm (1H, s)
d δ = 5.05 ppm (1H, d)
e δ = 4.8 ppm (1H, m)
f δ between 4.55 and 3.95 ppm (2H, m)
g δ = 3.55 ppm (3H, s)
h δ between 3.0 and 2.5 ppm (7H, m)
i δ between 1.6 and 1.4 ppm (6H, m)

EXAMPLE 30:
3-oxoBzAZEP-(S)(Nτ-Me)His-(1S,3S,4R)ABH-NH$_2$ "isomer"

The "B" isomer is obtained after elution of the "A" isomer of Example 29.

Proton Nuclear Magnetic Resonance (CDCl$_3$):

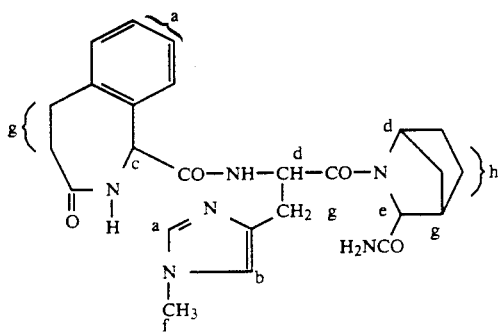

a δ between 7.4 and 7.2 ppm (5H, m)
b δ = 6.5 ppm (1H, s)
c δ = 5.0 ppm (1H, d)
d δ between 4.80 and 4.55 ppm (2H, m)
e δ = 3.95 ppm (1H, d)
f δ = 3.45 ppm (3H, s)
g δ between 3.1 and 2.4 ppm (7H, m)
h δ between 1.8 and 1.4 ppm (6H, m)

EXAMPLE 31: AZEP-Pyra-(1S,3S,4R)ABH-NH$_2$ "isomer A"

Stage A: Nα,NPyr-DiBoc(RS)Pyra-OH 43 mmol of (RS)Pyra-OH, described by R. G. JONES (J.A.C.S., 71, 3994–4000, 1949) are added to 100 ml of dioxane and 86 ml of 1N sodium hydroxide. After cooling to between 0° and 5° C., 18.8 g of di-tert-butyl dicarbonate in 50 ml of dioxane are added in the course of 30 minutes. Stirring is maintained for 20 hours at room temperature. The mixture is neutralized by adding 86 ml of 1N hydrochloric acid and taken to dryness. The residue is taken up with ethanol. After the sodium chloride is filtered off and the ethanol evaporated off, the residue is finally taken up with 150 ml of isopropyl ether. After filtration and evaporation, the expected product is obtained. Yield: 98%

Stage B: Nα,NPyr-DiBoc-Pyra-(1S,3S,4R)ABH-NH$_2$ "isomer α"

Using the peptide coupling technique described by W. KONIG and R. GEIGER (Chem. Ber., 103, 2034, 1970), the product obtained in the preceding stage is reacted with (1S,3S,4R)ABH-NH$_2$.

The "α" and "β" isomers are separated by chromatography on silican gel.

Stage C: Pyra-(1S,3S,4R)ABH-NH$_2$dihydrochloride "isomer α"

The product obtained in Stage B is dissolved in dioxane into which a stream of hydrochloric acid is passed for thirty minutes. The mixture is kept stirring for 20 hours. The expected product is obtained by filtration, then washed with dioxane and dried. Yield: ≈100%

Stage D: (RS)AZEP-Pyra-(1S,3S,4R)ABH-NH$_2$ "isomer α"

Using the procedure described in Stage B of Example 1, but replacing (S)(Nτ-Me)His-(1S,3S,4R)ABH-NH$_2$ dihydrochloride by the product obtained in the preceding stage, the expected product is obtained. Yield: 68%

Stage E: AZEP-Pyra-(1S,3S,4R)ABH-NH$_2$ "isomers A"

The mixture of isomers obtained in Stage D is separated by preparative liquid chromatography on C$_{18}$ silica, using a water/acetonitrile/acetic acid (95:5:0.1) mixture as eluent. The isomers designated "A" and "B" in order of emergence from the column are obtained in the form of acetates, which are converted to bases by passage through Amberlite IRA93 resin followed by evaporation and lyophilization.

Proton Nuclear Magnetic Resonance (DMSO-d$_6$):

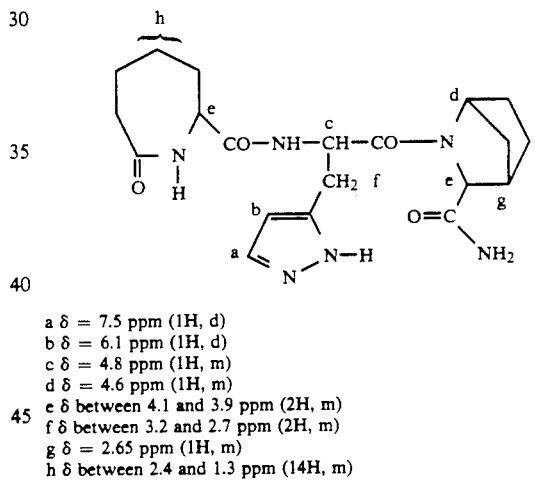

a δ = 7.5 ppm (1H, d)
b δ = 6.1 ppm (1H, d)
c δ = 4.8 ppm (1H, m)
d δ = 4.6 ppm (1H, m)
e δ between 4.1 and 3.9 ppm (2H, m)
f δ between 3.2 and 2.7 ppm (2H, m)
g δ = 2.65 ppm (1H, m)
h δ between 2.4 and 1.3 ppm (14H, m)

EXAMPLE 32: AZEP-Pyra-(1S,3S,4R)ABH-NH$_2$ "isomer B"

Stages A, B, C, D and E are identical to those of Example 31. The "B" isomer is obtained in Stage E after elution of the "A" isomer of Example 31.

| | Elemental microanalysis: | | |
| --- | --- | --- | --- |
| | C % | H % | N % |
| Calculated | 57.68 | 6.78 | 20.18 |
| Found | 57.54 | 6.61 | 19.91 |

EXAMPLE 33: AZEP-Pyra-(1S,3S,4R)ABH-NH$_2$ "isomer C"

Stages A, B, C, D and E are identical to those of Example 31, but the "β" isomer of Nα,NPyr-DiBoc-Pyra(1S,3S,4R)ABH-NH$_2$ is used in Stage C in place of the "α" isomer.

| | Elemental microanalysis: | | |
|---|---|---|---|
| | C % | H % | N % |
| Calculated | 57.68 | 6.78 | 20.18 |
| Found | 58.05 | 6.68 | 19.93 |

EXAMPLE 34: AZEP-Pyra-(1S,3S,4R)ABH-NH$_2$ "isomer D"

Stages A, B, C, D and E are identical to those of Example 33. The "D" isomer is obtained in Stage E after elution of the "C" isomer of Example 33.

| | Elemental microanalysis: | | |
|---|---|---|---|
| | C % | H % | N % |
| Calculated | 57.68 | 6.78 | 20.18 |
| Found | 58.00 | 6.58 | 20.23 |

EXAMPLES 35 to 38: AZEP-AmPyri-(1S,3S,4R)ABH-NH$_2$ "isomers A, B, C and D"

EXAMPLE 39: 1-oxoBzAZEP-(S)(Nτ-Me)His-(1S,3S,4R)ABH-NH$_2$ "isomer A"

Using the procedure described in Example 1, but replacing the ethyl ester of (RS)AZEP-OH in Stage A by the ethyl ester of (RS)-1-oxoBzAZEP-OH obtained from 2-carbethoxyα-tetralone described by I. UGI et al. (Ann., 641, 63-70, 1961), the expected product is obtained after separation of the isomers by liquid chromatography (C$_{18}$ silica column, elution solvent: water-/acetonitrile/diethylamine, 90:10:0.5).

Proton Nuclear Magnetic Resonance (DMSO-d$_6$):

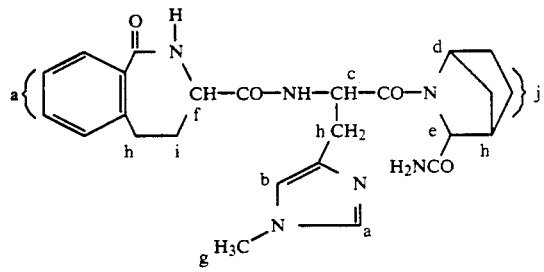

a δ between 7.5 and 7.2 ppm (5H, m)
b δ = 6.8 ppm (1H, s)
c δ between 4.75 and 4.6 ppm (1H, m)
d δ = 4.5 ppm (1H, m)
e δ = 3.9 ppm (1H, d)
f δ between 3.8 and 3.6 ppm (1H, m)
g δ = 3.55 ppm (3H, s)
h δ between 3.0 and 2.4 ppm (5H, m)
i δ between 2.3 and 1.8 ppm (2H, m)
j δ between 1.7 and 1.3 ppm (6H, m)

EXAMPLE 40: 1-oxoBzAZEP-(S)(Nτ-Me)His-(1S,3S,4R)ABH-NH$_2$ "isomer B"

The "B" is obtained after elution of the "A" isomer of Example 39.

Proton Nuclear Magnetic Resonance (DMSO-d$_6$):

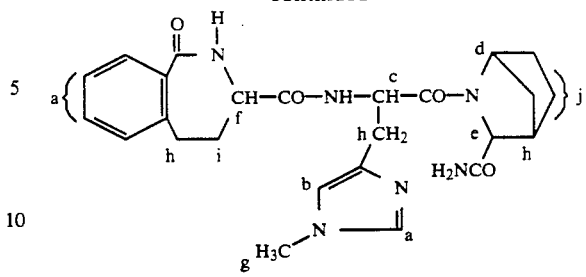

a δ between 7.5 and 7.2 ppm (5H, m)
b δ = 6.8 ppm (1H, s)
c δ between 4.75 and 4.6 ppm (1H, m)
d δ = 4.5 ppm (1H, m)
e δ = 3.9 ppm (1H, d)
f δ between 3.8 and 3.6 ppm (1H, m)
g δ = 3.55 ppm (3H, s)
h δ between 3.0 and 2.4 ppm (5H, m)
i δ between 2.3 and 1.8 ppm (2H, m)
j δ between 1.7 and 1.3 ppm (6H, m)

EXAMPLES 41 and 42: 2-oxoBzAZEP-(S)(Nτ-Me)His-(1S,3S,4R)-ABH-NH$_2$ "isomers A and B"

EXAMPLES 43 and 44: AZON-(S)(Nτ-Me)His-(1S,3S,4R)ABH-NH$_2$ "isomers A and B"

EXAMPLES 45 and 46: AZEC-(S)(Nτ-Me)His-(1S,3S,4R)ABH-NH$_2$ "isomers A and B"

EXAMPLE 47: AZEC-(S)(Nτ-Me)His-(1S,3S,4R)ABO-NH$_2$ "isomer A"

The expected product is obtained using the procedure described in Example 1, but replacing (1S,3S,4R)ABH-NH$_2$ by (S)ABO-NH$_2$.

The "A" and "B" isomers are separated by liquid chromatography (C$_{18}$ silica column, elution solvent: water/methanol/diethylamine, 80:20:0.1).

Proton Nuclear Magnetic Resonance (DMSO-d$_6$):

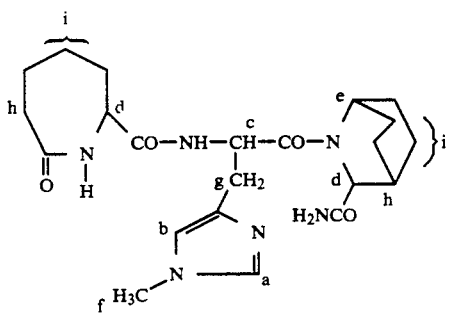

a δ = 7.5 ppm (1H, s)
b δ = 6.9 ppm (1H, s)
c δ = 4.85 ppm (1H, m)
d δ = 4.05 ppm (2H, m)
e δ = 3.8 ppm (1H, m)
f δ = 3.6 ppm (3H, s)
g δ between 3.0 and 2.6 ppm (2H, m)
h δ between 2.4 and 2.1 ppm (3H, m)
i δ between 2.0 and 1.3 ppm (1H, m)

EXAMPLE 48:
AZEP-(S)(Nτ-Me)His-(S)ABO-NH₂ "isomer B"

The "B" isomer is obtained after elution of the "A" isomer of Example 47.

Proton Nuclear Magnetic Resonance (DMSO-d₆):

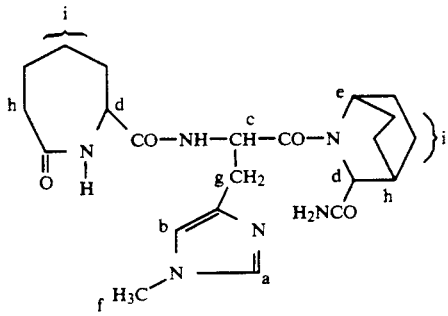

a δ = 7.5 ppm (1H, s)
b δ = 6.9 ppm (1H, s)
c δ = 4.85 ppm (1H, m)
d δ = 4.05 ppm (2H, m)
e δ = 3.8 ppm (1H, m)
f δ = 3.6 ppm (3H, s)
g δ between 3.0 and 2.6 ppm (2H, m)
h δ between 2.4 and 2.1 ppm (3H, m)
i δ between 2.0 and 1.3 ppm (1H, m)

EXAMPLE 49:
AZEP-(S)(Nτ-Me)His-(2S,3aS,7aS)PHI-NH₂ "isomer A"

The expected product is obtained using the procedure described in Example 1, but replacing (1S,3S,4R)ABH-NH₂ by (2S,3aS,7aS)PHI-NH₂.

The "A" and "B" isomers are separated by liquid chromatography (C₁₈ silica column, elution solvent: water/acetonitrile/acetic acid, 97.5:2.5:0.1).

| | Elemental microanalysis: | | |
|---|---|---|---|
| | C % | H % | N % |
| Calculated | 60.24 | 7.47 | 18.33 |
| Found | 60.66 | 7.33 | 18.06 |

EXAMPLE 50:
AZEP-(S)(NτMe)His-(2S,3aS,7aS)PHI-NH₂ "isomer B"

The "B" isomer is obtained after elution of the "A" isomer of Example 49.

| | Elemental microanalysis: | | |
|---|---|---|---|
| | C % | H % | N % |
| Calculated | 60.24 | 7.47 | 18.33 |
| Found | 60.34 | 7.17 | 17.91 |

EXAMPLE 51: AZEP-(S)(Nτ-Me)His-THIQ-NH₂

EXAMPLE 52: AZEP-(S)(Nτ-Me)His-ThiaPro-NH₂

PHARMACOLOGY STUDY OF THE COMPOUNDS OF THE INVENTION

EXAMPLE 53: Cholinergic deficit induced by barbiturate narcosis in mice

In mice, pentobarbital (60 mg/kg IP) narcosis leads in the hippocampus to a very pronounced (−70%) and reproducible deficit in sodium-dependent choline uptake (HACU). The decrease in this limiting factor in acetylcholine synthesis is evidence of the inhibition of cholinergic neurotransmission, a system closely involved in mnestic functions.

When administered simultaneously with pentobarbital, TRH counteracts the fall in HACU (10 mg/kg IP:−35%), which is no longer the case if it is administered 30 minutes before pentobarbital (10 mg/kg IP:−1.9%; 30 mg/kg IP:+4.8%). In contrast, the compounds of the invention very significantly counteract the fall in HACU, even if they are administered IP 30 minutes before the induction of narcosis:
Compound of Example 1:
  (3 mg/kg):−61.1%
  (1 mg/kg):−25.5%
Compound of Example 5: (0.3 mg/kg):−31.1%
Compound of Example 10: (1 mg/kg):−50.8%

EXAMPLE 54: Oxotremorine-induced tremor in mice

Administered at a dose of 0.5 mg/kg IP, oxotremorine, a non-selective $M_1$–$M_2$ muscarinic agonist leads to cholinergic symptoms of central origin, such as tremor. In control animals, the maximum tremor-inducing effect is observed after 15 minutes, and this effect disappears completely in the course of 45 to 60 minutes.

The administration of TRH (10 mg/kg IP) 30 minutes before that of oxotremorine potentiates the tremor (+50%) at its peak of intensity (15 minutes), but prolongs it to only a very small extent (15 minutes:+20%). The minimal active dose is 5 mg/kg.

Under the same conditions, the compounds of the invention also exert the same potentiating effect, but at much lower minimal active doses, and this effect persists for a further 60 minutes after the injection of oxotremorine. Thus, the minimal active doses are, for example, as follows:
Compound of Example 1: 0.3 mg/kg
Compound of Example 5: 0.1 mg/kg When the time elapsing between the administration of the product under study and that of oxotremorine is extended, TRH no longer potentiates the tremor measured at the peak if it is administered 60 minutes before the muscarinic agonist, whereas the compounds of the invention remain active even when administered 150 minutes beforehand.

EXAMPLE 55: Xylazine induced inhibition of the righting reflex in rats

The administration of a central $\alpha_2$ agonist, xylazine, to rats leads to loss of the animal's righting reflex. This effect is antagonized by yohimbine ($\alpha_2$ antagonist) and by agents facilitating noradrenaline release.

TRH antagonizes the effect of xylazine, and the median effective dose is close to 10 mg/kg IP. Under the same conditions, the $ED_{50}$ of the compounds of Examples 1 and 5 are 0.1 and 0.3 mg/kg, respectively.

The compounds of the invention hence facilitate noradrenergic neurotransmission when the latter is previously inhibited.

PHARMACEUTICAL COMPOSITION

EXAMPLE 56:

Preparation formula for 1000 tablets containing 10 mg of the compound of Example 1:

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from these of formula (I):

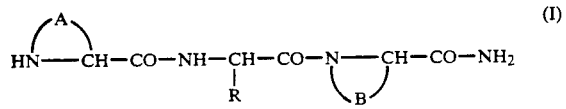

in which:
A represents, with the nitrogen and carbon atoms to which it is linked:
  a 2-oxoperhydro-7-azepinyl group
  a 2-oxoperhydro-8-azocinyl group
  a 2-oxoperhydro-9-azoninyl group
  a 2-oxoperhydro-10-azecinyl group
  a 2-oxo-2,3,4,7-tetrahydrobenz[e]azepin-7-yl group
  a 2-oxo-2,3,6,7-tetrahydrobenz[d]azepin-7-yl group
  a 2-oxo-2,5,6,7-tetrahydrobenz[c]azepin-7-yl group
B represents, with the nitrogen and carbon atoms to which it is linked, a polycyclic structure selected from the following structures:
  2-azabicyclo[2.2.1]heptane,
  2-azabicyclo[2.2.2]octane, optionally substituted at positions 1 and 4 with a linear or branched ($C_1$–$C_4$) alkyl group,
  perhydroindole,
  perhydroisoindole,
  indoline,
  isoindoline,
  perhydroquinoline,
  perhydroisoquinoline,
  1,2,3,4-tetrahydroquinoline,
  1,2,3,4-tetrahydroisoquinoline,
  cyclopenta[b]pyrrolidine,
  pyrrolidine, optionally substituted with one or two linear or branched ($C_1$–$C_4$) alkyl group,
  piperidine,
  thiazolidine,
R represents:
  hydrogen,
  linear or branched ($C_1$–$C_6$) alkyl optionally substituted with amino or guanidino,
  (4-imidazolyl)methyl optionally substituted on one of the nitrogen atoms with linear or branched ($C_1$–$C_4$) alkyl,
  (3-pyrazolyl)methyl,
  (2-pyridyl)methyl optionally substituted with amino,
its enantiomers, diastereoisomers and epimers, as well as its addition salts with a pharmaceutically-acceptable acid.

2. A compound as claimed in claim 1 selected from those wherein A, with the nitrogen and carbon atoms to which it is linked, forms a 2-oxoperhydroazepine ring, its enantiomers, diastereoisomers and epimers as well as its addition salts with a pharmaceutically acceptable acid.

3. A compound as claimed in claim 1 selected from those wherein B, with the nitrogen and carbon atoms to which it is linked, forms a 2-azobicyclo[2.2.1]heptane ring, its enantiomers, diastereoisomers and epimers as well as its addition salts with a pharmaceutically-acceptable acid.

4. The compound as claimed in claim 1 which is selected from AZEP-(Nτ-Me)His-ABH-$NH_2$, its enantiomers, diastereoisomers and epimers as well as its addition salts with a pharmaceutically-acceptable acid, AZEP representing a 7-carbonylperhydro-2-azepinone radical, (Nτ-Me)His a 1-methylhistidyl radical, and ABH a 2-aza-3-carbonylbicyclo [2.2.1]heptane radical.

5. The compound as claimed in claim 1 which is selected from AZEP-(S)His-(S)Pro-$NH_2$, its enantiomers, diastereoisomers and epimers as well as its addition salts with a pharmaceutically-acceptable acid, AZEP representing a 7-carbonylperhydro-2-azepinone radical, His a histidyl radical, and Pro a prolyl radical.

6. A method of treating a living animal or human afflicted with a disease resulting from a cognitive disorder or a neuro-behavioral disorder associated with aging, or an acute or chronic degenerative disease comprising the step of administering to the said living animal or human an amount of a compound of claim 1 which is effective for alleviation of said condition.

7. A pharmaceutical composition useful in the treatment of a disease resulting from a cognitive disorder, a neuro-behavioral disorder associated with aging, or an acute or chronic degenerative disease, comprising as active principle an effective amount of a compound as claimed in claim 1 in combination with a pharmaceutically-acceptable excipient or vehicle.

* * * * *

UNITED STATES PATENT AND TRADEMARK OFFICE
CERTIFICATE OF CORRECTION

PATENT NO. : 5,190,923

DATED : Mar. 2, 1993

INVENTOR(S) : Michel Vincent, Georges Remond, Bernard Portevin, Yolande Herve, Jean Lepagnol It is certified that error appears in the above-indentified patent and that said Letters Patent is hereby corrected as shown below:

Column 3, approximately line 11; "acetate the" should read --acetate in the--.
Column 4, line 52; "an $a_2$ agonist," should read --an $\alpha_2$ agonist,--.
Column 6, approximately line 27; "Lys/τ " should read -- -Lys/z --.
Column 7, line 15; "(c=2%, ethanol)" should read -- (C = 1%, ethanol) --.
Column 13, approximately line 30; "e 60" should read -- e $S$ --.
Column 14, approximately line 42; above "Elemental microanalysis:" insert -- Yield: 87% --.
Column 15, approximately line 4; above "Elemental microanalysis:" insert -- Yield: 91% --.
Column 15, approximately line 13; change ""isomer"" to --"isomer B" --.
Column 17, line 7; ""A"" and ""A"" should read -- "A" and "B" --.
Column 19, approximately line 13; ""isomer"" should read -- "isomer B" --.
Column 21, approximately line 32; "2-carbethoxy $\alpha$ -" should read -- 2-carbethoxy-$\alpha$ - --.
Column 22, line 35; "AZEC-" should read -- AZEP- --.
Column 22, line 35; "(1S,3S,4R)ABO-$NH_2$" should read -- (S)ABO-$NH_2$ --.

Signed and Sealed this

Eighth Day of February, 1994

Attest:

BRUCE LEHMAN

Attesting Officer     Commissioner of Patents and Trademarks